(12) United States Patent
Leach et al.

(10) Patent No.: US 9,000,155 B2
(45) Date of Patent: *Apr. 7, 2015

(54) CYCLIC TRIAZO SODIUM CHANNEL BLOCKERS

(71) Applicant: University of Greenwich, London (GB)

(72) Inventors: Michael Leach, Chatham Kent (GB); Karl Franzmann, Chatham Kent (GB); Dieter Riddall, Chatham Kent (GB); Laurence Harbige, Chatham Kent (GB)

(73) Assignee: University Of Greenwich, London Greater London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/266,398

(22) Filed: Apr. 30, 2014

(65) Prior Publication Data
US 2014/0243343 A1    Aug. 28, 2014

Related U.S. Application Data

(63) Continuation of application No. 13/382,720, filed as application No. PCT/GB2010/051126 on Jul. 8, 2010, now Pat. No. 8,748,599.

(30) Foreign Application Priority Data

Jul. 8, 2009 (GB) .................................. 0911991.8
Jul. 9, 2009 (GB) .................................. 0911925.6
Jul. 15, 2009 (GB) .................................. 0912271.4

(51) Int. Cl.
| | |
|---|---|
| C07D 253/07 | (2006.01) |
| A61K 31/53 | (2006.01) |
| A61P 25/08 | (2006.01) |
| A61P 25/28 | (2006.01) |
| A61P 25/04 | (2006.01) |
| C07D 253/075 | (2006.01) |
| C07D 409/04 | (2006.01) |
| C07D 309/04 | (2006.01) |
| C07D 309/06 | (2006.01) |
| C07D 309/08 | (2006.01) |

(52) U.S. Cl.
CPC .......... C07D 253/075 (2013.01); C07D 253/07 (2013.01); C07D 409/04 (2013.01); C07D 309/04 (2013.01); C07D 309/06 (2013.01); C07D 309/08 (2013.01)

(58) Field of Classification Search
CPC ............. C07D 253/075; C07D 403/04; C07D 405/04; C07D 409/04; A61K 31/53
USPC .......................................... 544/182; 514/242
See application file for complete search history.

(56) References Cited

U.S. PATENT DOCUMENTS

| | | | |
|---|---|---|---|
| 8,268,823 B2 * | 9/2012 | Leach et al. ................... | 514/242 |
| 8,691,818 B2 * | 4/2014 | Leach et al. ................... | 514/242 |
| 8,748,599 B2 * | 6/2014 | Leach et al. ................... | 544/182 |
| 8,748,600 B2 * | 6/2014 | Leach et al. ................... | 544/182 |

* cited by examiner

*Primary Examiner* — Venkataraman Balasubramanian
(74) *Attorney, Agent, or Firm* — Cesari and McKenna, LLP

(57) ABSTRACT

The present invention relates to triazine compounds having sodium channel blocking properties, and to use of the compounds for preparation of medicaments for treatment of associated disorders. The compounds are of formula I:

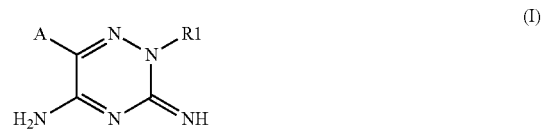

(I)

in which R1 is a halo-alkyl group and A is an optionally substituted aromatic heterocyclic or carbocyclic ring system, or a pharmaceutically acceptable salt or solvate thereof.

21 Claims, No Drawings

CYCLIC TRIAZO SODIUM CHANNEL BLOCKERS

This application is a continuation of U.S. application Ser. No. 13/382,720, filed on Feb. 14, 2012, which is a National Stage of International Application No. PCT/GB2010/051126, filed on Jul. 8, 2010, which claims priority from Great Britain Application No. 0911991.8, filed on Jul. 8, 2009, Great Britain Application No. 0911925.6, filed on Jul. 9, 2009, and Great Britain Application No. 0912271.4, filed on Jul. 15, 2009. The contents of these applications are incorporated herein by reference in their entireties.

The present invention relates to triazine compounds having sodium channel blocking properties, and to use of the compounds for preparation of medicaments for treatment of associated disorders.

U.S. Pat. No. 4,649,139 discloses compounds of the formula (A):

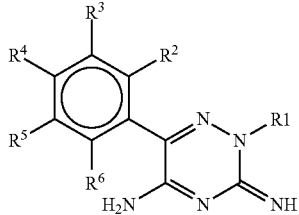

(A)

in which $R^1$ is $C_{1-10}$ alkyl, $C_{2-10}$ alkenyl, $C_{2-10}$ alkynyl or $C_{3-10}$ cycloalkyl, any of which is optionally substituted, and $R^2$ to $R^6$ are independently selected from hydrogen, halogen, $C_{1-6}$ alkyl, alkenyl, alkynyl or alkoxy (all optionally substituted by one or more of halogen, hydroxy and aryl), amino, mono- or di-substituted amino, alkenyloxy, acyl, acyloxy, cyano, nitro, aryl and alkylthio groups or any adjacent two of $R^2$ to $R^6$ are linked to form a (—CH=CH—CH=CH—) group. It is disclosed that these compounds are active in the treatment of cardiac disorders, and are particularly useful in the treatment of arrhythmias.

Our previous patent application WO2008/007149 discloses uses of a compound of formula (B):

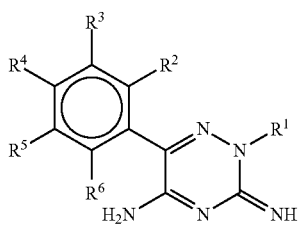

(B)

in which $R^1$ is hydrogen (and =NH is $NH_2$), or is carboxamido, $C_{1-10}$ alkyl, $C_{2-10}$ alkenyl, $C_{1-3}$ alkyl-aryl, $C_{1-3}$ alkyl-heterocyclyl, or $C_{3-10}$ cycloalkyl, any of which is optionally substituted by hydroxy, halogen, carboxamido, halo $C_{1-6}$ alkyl, $C_{1-6}$ alkyl or $C_{1-6}$ alkoxy; and $R^2$ to $R^6$ are independently selected from hydrogen, halogen, $C_{1-6}$ alkyl, alkenyl, alkynyl or alkoxy (all optionally substituted by one or more of halogen, hydroxy and aryl), amino, mono- or di-substituted amino, alkenyloxy, acyl, acyloxy, cyano, nitro, aryl and alkylthio groups;

(a) as voltage-dependent sodium channel blockers for the treatment of disorders in mammals, and particularly epilepsy, multiple sclerosis, glaucoma and uveitis, cerebral traumas and cerebral ischaemias, stroke, head injury, spinal cord injury, surgical trauma, neurodegenerative disorders, motor neurone disease, Alzheimers disease, Parkinsons disease, chronic inflammatory pain, neuropathic pain, migraine, bipolar disorder, mood, anxiety and cognitive disorders, schizophrenia and trigeminal autonomic cephalalgias, especially in humans; and (b) as antifolates for the treatment of disorders in mammals, and particularly for treatment of mammalian cancers and as antimalarials against *plasmodium vivax* and *plasmodium falciparum* malaria, especially in humans.

According to the present invention there are provided compounds of formula (I):

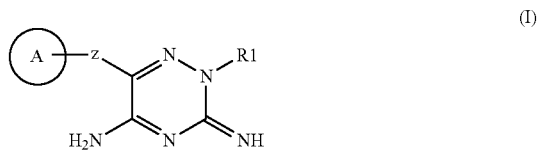

(I)

in which Z is a single bond or an optionally substituted linking group;

R1 is a halo-alkyl group; and

A is an (optionally substituted) aromatic heterocyclic or carbocyclic ring system.

Ring system A may comprise any number of ring components.

The aromatic carbocyclic ring system is typically phenyl, optionally substituted phenyl.

The aromatic heterocyclic ring system is typically (benzo)thienyl or (benzo)furyl or (benzo)pyran or (iso)indole or (iso)quinoline or pyridine, optionally substituted.

Preferably, R1 is $C_{1-10}$ halo-alkyl. More preferably, R1 is methyl, ethyl, i-propyl, n-propyl, butyl or n-butyl, substituted by one or more halogen, preferably chloro, bromo or fluoro. Most preferably, R1 is di- or tri-halo substituted (especially chloro and/or fluoro).

Suitably, Z is a linking group comprising a carbon atom with one or two optionally substituted alkyl or phenyl groups.

Preferably, A is an aromatic carbocyclic ring system, such as phenyl, naphthyl, anthracenyl or fluorenyl, optionally substituted with one or more halogens, such as chloro, bromo or fluoro; or fluoroalkyl, such as CF3; alkoxy, such as methoxy or ethoxy; and/or aryloxy, such as phenoxy or benzyloxy.

In one group, A is selected from chlorophenyl, such as dichlorophenyl or trichlorophenyl, for example 2,3-, 2,6- and 3,5-dichloro-, and 2,3,5-trichloro phenyl; bromophenyl such as 2-bromo- and 3-bromo phenyl; trifluoromethyl phenyl such as di-trifluoromethyl, for example 3,5-trifluoromethyl; (m) ethoxy phenyl such as di(m)ethoxy- and tri(m)ethoxyphenyl, for example 4,5 dimethoxy phenyl, 3,4,5 trimethoxy phenyl; fluoro(m)ethoxy phenyl such as di(fluoro(m)ethoxy) phenyl, for example 2-fluoro(m)ethoxy, 4-fluoro(m)ethoxy and 2,4-di(fluoro(m)ethoxy) phenyl.

In a further group, A is a bicyclic group. Suitably, the bicyclic group is selected from naphthyl, such as 1-naphthyl and 2-naphthyl or tetrahydronaphthyl; or alkylenedioxyphenyl, such as (m)ethylenedioxyphenyl or benzodioxolo. The group may be substituted, for example by one or more halogens such as bromo, for example 6-bromonaphthyl; or fluoro, for example 2,2-difluorobenzodioxolo; or by one or more alkoxy groups such as (m) ethoxy for example 2- or 3-(m)ethoxynaphthyl or 1,4-, 2,5- or 3,7-di(m)ethoxynaphthyl.

In a yet further group A is a tricyclic group. The tricyclic group is suitably a fused ring system containing one or more aromatic rings, such as anthracenyl or fluorenyl; or non-aromatic rings such as adamantyl, optionally substituted as described above.

In a further group, A is a bis-cyclic group comprising two ring substituents of any of the ring systems described above.

In one class of compounds of formula (I), substituents on the A ring include phenyl and phenoxy, benzyl and benzyloxy, optionally substituted on the phenyl ring with halogen or alkoxy or other substituents as described above.

In a further class of compounds, A is an optionally substituted heterocyclic ring system; for example, a monocyclic or bicyclic heterocyclic group with one or more oxygen or sulphur or nitrogen atoms; especially an aromatic heterocyclic ring system.

Suitably, compounds of formula (I) in which A is a heterocyclic group are compounds of formula (II):

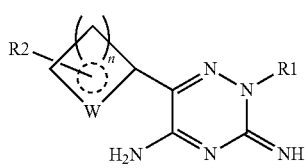

(II)

in which W is sulphur, oxygen or nitrogen and n is 1, 2 or 3, and R3 is one or more substituent.

Suitably, the heterocyclic group is (i) a sulphur-containing heterocycle selected from thienyl and benzothienyl groups; (ii) an oxygen-containing heterocycle selected from furyl, phenylfuryl and benzopyranyl; or a nitrogen-containing heterocycle selected from pyridyl, indolyl, quinolyl and isoquinolyl. Advantageously, substituted as for the structures described above; for carbocyclic A rings, for example by halogen, alkyl or alkoxy, especially by 1, 2 or 3 chlorine or bromine atoms. Nitrogen-containing heterocycles are optionally N-substituted by alkyl such as methyl, or substituted by phenoxy or phenylthio, with the phenyl optionally substituted by halogen such as chloro.

Optionally, heterocyclic ring A is a bis-heterocyclic compound.

In one embodiment, the compounds of formula (I) are compounds of formula (III):

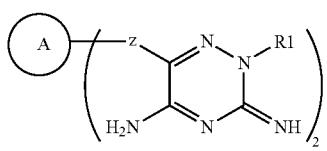

(III)

This embodiment encompasses compounds in which two compounds of formula (I) share a common A ring; and compounds of a bis-ring structure.

The present invention also provides salts of any of the above compounds. Preferred salts are pharmaceutically acceptable acid addition salts. Suitable pharmaceutically acceptable acid addition salts include those formed with both organic and inorganic acids, for example from hydrochloric, sulphuric, citric, tartaric, phosphoric, lactic, pyruvic, acetic, malonic, succinic, oxalic, fumaric, maleic, oxaloacetic, methanesulphonic, p-toluenesulphonic, benzene-sulphonic, glutamic, naphthoic, and isethionic acids. Ethanesulphonate, malate, mandalate, benzoate, and salicylate salts are also suitable.

The present invention also provides solvates of any of the compounds of formula (I) or salts thereof. The compound or its salt may be obtained as a solvate of the reaction solvent or crystallisation solvent or a component thereof in preparation of the compound. Suitable pharmaceutically acceptable solvates include hydrates.

Compounds of formula (I) may have chiral centres and may occur as racemates, racemic mixtures and as individual enantiomers or diastereomers. All such isomeric forms are included within the present invention. Also included within the scope of the invention are all geometric isomers of the compound of formula (I) whether as individual isomers or mixtures thereof. Thus compounds of formula (I) in the trans- and cis-configuration are encompassed by the present invention; as are tautomeric forms and mixtures thereof, and polymorphic crystalline forms.

Certain compounds of formula (I) may be prepared by the procedures disclosed in the above-mentioned U.S. Pat. No. 4,649,139, the entire disclosure of which is incorporated herein by reference and to which further reference should be made. Certain compounds of formula (I) may also be prepared by methods disclosed in EP 0 021 121 A, the entire disclosure of which is incorporated herein by reference and to which further reference should be made.

The preparation of specific compounds mentioned above is illustrated later in this specification. Related compounds within the scope of the invention may be prepared by obvious or routine variations of the disclosed processes, using appropriate starting materials to introduce the desired substituents and moieties of compounds within the scope of formula (I).

Salts of compounds of formula (I) may be obtained by the presence of a residual acid in the preparative process. Alternatively salts may be prepared by mixing the compound of formula (I) as the free base with a pharmaceutically acceptable acid in a suitable solvent, and removing the solvent to recover the salt, or crystallising the salt from the solvent.

In a further aspect, the present invention provides pharmaceutical compositions comprising a compound of formula (I) or a pharmaceutically acceptable salt or solvate thereof, in admixture with a pharmaceutically acceptable carrier. The compounds are suitable for the treatment of disorders such as epilepsy, multiple sclerosis, glaucoma and uveitis, cerebral traumas and cerebral ischaemias, stroke, head injury, spinal cord injury, surgical trauma, neurodegenerative disorders, motor neurone disease, Alzheimers disease, Parkinsons disease, chronic inflammatory pain, neuropathic pain, migraine, bipolar disorder, mood, anxiety and cognitive disorders, schizophrenia and trigeminal autonomic cephalalgias; for treatment of mammalian cancers; and for treatment of malaria.

The compounds of formula (I) are present in the compositions of the present invention in an effective unit dosage form, that is to say in an amount sufficient to be effective against the disorders in vivo.

The pharmaceutically acceptable carriers present in the compositions of the present invention may be materials conventionally used for the purpose of administering the medicament. These may be liquid or solid materials, which are otherwise inert or medically acceptable and are compatible with the active ingredients.

These pharmaceutical compositions may be given orally or parenterally, for example as a suppository, ointment, cream, powder or trans-dermal patch. However, oral administration and intravenous injection of the compositions are preferred.

For oral administration, fine powders or granules will contain diluting, dispersing and/or surface active agents, and may be presented in draught, in water or in a syrup, in capsules or sachets in the dry state or in non-aqueous suspension wherein suspending agents may be included, or in a suspension in water or syrup. Where desirable or necessary, flavouring, preserving, suspending, or thickening agents can be included. Dry powders or granules may be compressed to form a tablet or contained in a capsule.

For injection, the compounds may be presented in sterile aqueous injection solutions which may contain anti-oxidants or buffers.

The free base or a salt or solvate thereof may also be administered in its pure form unassociated with other additives in which case a capsule or sachet is the preferred carrier.

Alternatively the active compound is presented in a pure form at an effective unit dosage, for instance compressed as a tablet or the like.

Other compounds which may be included are, for example, medically inert ingredients, e.g., solid and liquid diluents such as lactose, starch, or calcium phosphate for tablet or capsules; olive oil or ethyl oleate for soft capsules; and water or vegetable oil for suspensions or emulsions; lubricating agents such as talc or magnesium stearate; gelling agents such as colloidal clays; thickening agents such as gum tragacanth or sodium alginate; and other therapeutically acceptable accessory ingredients such as humectants, preservatives, buffers, and antioxidants which are useful as carriers in such formulations.

Tablets or other forms of presentation provided in discrete units may conveniently contain an amount of compound of formula I which is effective at such dosage or as a multiple of the same, for instance units containing 5 mg to 500 mg, usually around 10 mg to 250 mg.

The pharmaceutical compositions of the present invention may be prepared by the admixture of a compound of formula (I) with a pharmaceutically acceptable carrier. Conventional pharmaceutical excipients may be admixed as required. Example of suitable formulations are give in the above-mentioned U.S. Pat. No. 4,649,139.

The present invention provides a method of treatment by the administration of a non-toxic effective amount of a compound of formula (I) or a pharmaceutically acceptable salt or solvate thereof, or a composition as hereinbefore defined. The method is particularly suitable for the treatment of disorders in mammals that are susceptible to sodium channel blockers and antifolates, and particularly disorders such epilepsy, multiple sclerosis, glaucoma and uveitis, cerebral traumas and cerebral ischaemias, stroke, head injury, spinal cord injury, surgical trauma, neurodegenerative disorders, motor neurone disease, Parkinsons disease, chronic inflammatory pain, neuropathic pain, migraine, bipolar disorder, mood, anxiety and cognitive disorders, schizophrenia and trigeminal autonomic cephalalgias; for treatment of mammalian cancers; and for treatment of malaria.

The present invention also provides a compound of formula (I) or a pharmaceutically acceptable salt or solvate thereof, or a composition as hereinbefore defined for, or for the preparation of a medicament. The medicament is particularly suitable for treatment of disorders in mammals that are susceptible to sodium channel blockers and antifolates, and particularly disorders such epilepsy, multiple sclerosis, glaucoma and uveitis, cerebral traumas and cerebral ischaemias, stroke, head injury, spinal cord injury, surgical trauma, neurodegenerative disorders, motor neurone disease, Alzheimer's disease, Parkinson's disease, chronic inflammatory pain, neuropathic pain, migraine, bipolar disorder, mood, anxiety and cognitive disorders, schizophrenia and trigeminal autonomic cephalalgias; for treatment of mammalian cancers; and for treatment of malaria.

As indicated above, the compounds of formula (I) are generally useful in treating such disorders by oral administration or intravenous injection.

The compounds of formula (I) are normally administered at a dose of from 0.01 mg/kg to 20 mg/kg per day, preferably 0.1 to 5.0 mg/kg per day.

In view of the known use in humans of structurally similar compounds such as lamotrigine, and other known compounds within the scope of formula (I) no major toxicity problems are anticipated in use of compounds of formula (I). However appropriate testing procedures should be carried out before clinical use.

The above and other aspects of the present invention will now be illustrated in further detail with reference to the accompanying examples.

The methodology for preparation of illustrative compounds of formula (I) and other compounds used in testing, is reported below. This may be adapted to prepare analogous compounds with additional or alternative substituents or moieties mentioned herein.

In the procedures below all melting points are in ° C.

3,5-Diamino-6-Aryl-1,2,4-triazine compounds

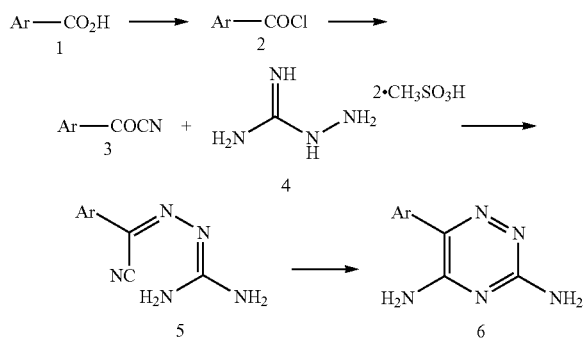

3,4-Dimethoxybenzoyl cyanide (3; Ar=3,4-dimethoxyphenyl)

A well stirred mixture [paddle stirrer] of 3,4-dimethoxybenzoyl chloride [AcrosOrganics] (14.05 g; 0.070 mol), dry toluene (32 cm$^3$), dry acetonitrile (8.0 cm$^3$), copper I cyanide (8.5; 0.095 mol) and Celite (5 g) was heated under reflux until no acid chloride remained (~1.5 hrs). The dark reaction mixture was cooled to ~70° and diluted with toluene (150 cm$^3$). After stirring for an additional ~30 minutes, the resulting slurry was filtered through a bed of chromatographic silica gel (~2.5 cm) and the pale yellow filtrate evaporated in vacuo to constant weight to give the title compound as a lemon yellow solid. Yield=11.41 g (85.3%), Mpt=143-145° C. The product was used directly in next stage.

Aminoguanidine bismesylate 4

To a stirred solution of 99.5% methanesulphonic acid [Aldrich] (422 g; 4.40 mol) in methanol (720 cm$^3$) at 40° was added portionwise over 30 minutes aminoguanidine bicarbonate [Aldrich] (272.0 g; 2.00 mol). When the addition was complete, the solution was stirred until the temperature had fallen to ~40° and then treated slowly with cold ether (500 cm³). During the addition, colourless needles started to deposit. The resulting slurry was stood at 0° for 4 hrs, filtered and the product washed with cold ether and dried overnight in vacuo at 50°. Yield=528 g (99.25%), mpt=149-150° (Lit: WO/2004/026845; 147.5°)

Schiffs Base, cyanohydrazone (5, Ar=3,4-dimethoxyphenyl)

To a stirred solution of aminoguanidine bismesylate (14.0 g; 0.053 mol) in 99.5% methanesulphonic acid (22 g) at 65-70° was added dropwise a warm solution of 3,4-dimethoxybenzoyl cyanide (5.7 g; 0.030 mol) in acetonitrile (30 cm³) over ~25 minutes. The mixture was then stirred at 68° until a sample gave a clear solution in water (~2.5 hrs) and then poured onto crushed ice/water (125 g) giving a pale yellow precipitate. The stirred mixture was neutralised (pH 8-9) with 48% sodium hydroxide (19.0 cm³) giving a bright yellow precipitate. The product was filtered, washed with cold water and dried in vacuo at 45°. Yield=6.21 g (83.8%), Mpt=98-100° C., TLC [SiO₂ plate, 10% methanol in chloroform], $R_f$=0.52. The product was used directly in the next stage.

6-Alkyl/Aralkyl-3,5-diamino-1,2,4-triazine Compounds

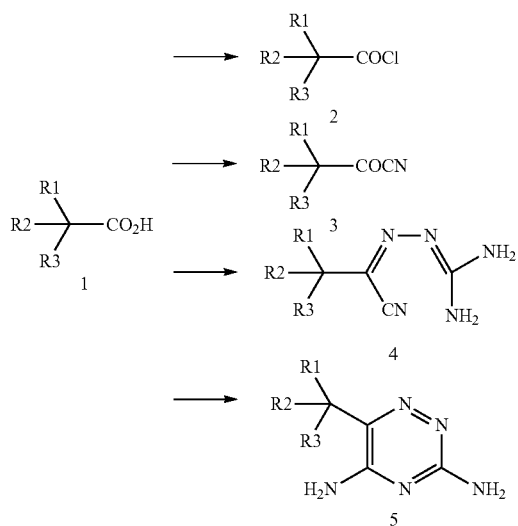

Triphenylacetyl chloride [3; $R_1=R_2=R_3$=Ph]

A stirred mixture of triphenylacetic acid (21.7 g; 0.075 mol) and dry dimethylformamide (2 drops) in dry dichloromethane (100 cm³) was treated with oxalyl chloride (14 g; 0.11 mol) which was added in 4 approximately equal portions over ~25 minutes. The mixture was stirred at 35° until evolution of hydrogen chloride had ceased (~4 hrs). The resulting colourless solution was evaporated in vacuo at 40° to constant weight to give the title compound as a colourless crystalline solid. Yield=23.24 g (100.0%). The product was used directly in next stage.

Similarly prepared were:

Triphenylacetyl cyanide [4; $R_1=R_2=R_3$=Ph]

A well stirred mixture [paddle stirrer] of triphenylacetyl cyanide (23.24 g; 0.075 mol), dry toluene (40 cm³), dry acetonitrile (10 cm³), copper I cyanide (9.20 g; 0.103 mol), Celite (3.5 g) and finely powdered potassium iodide (2 g) was heated under reflux until no acid chloride remained (~18 hrs). The dark reaction mixture was cooled to ~75° and diluted with toluene (150 cm³). After stirring for an additional ~30 minutes, the resulting slurry was filtered through a bed of chromatographic silica gel (~2.5 cm) and the colourless filtrate evaporated in vacuo to constant weight to give the title compound as a colourless solid. Yield=21.97 g (98.7%), Mpt=67-69°. The product was used directly in next stage.

Schiffs Base, cyanohydrazone, (4; $R_1=R_2=R_3$=Ph]

To a stirred solution of aminoguanidine bismesylate (15.00 g; 0.0564 mol) in 99.5% methanesulphonic acid (22.5 g) at 65-70° was added dropwise a solution of Triphenylacetyl cyanide (8.91 g; 0.030 mol) in acetonitrile (25 cm³) over ~25 minutes. The mixture was then stirred at 68° until a sample gave a clear solution in water (~28 hrs) and then poured onto crushed ice/water (150 g) giving a semi-solid colourless precipitate. The mixture was neutralised (pH 8-9) with 48% sodium hydroxide (17.5 cm³) giving the title compound as cream granular solid. The product was filtered off, washed with water and dried in vacuo at 45°. Yield=8.47 g (80.0%), Mpt=112-114°, TLC [SiO₂ plate, 10% methanol in chloroform], $R^f$=0.68. The product was used directly in the next stage.

Triazine Compounds

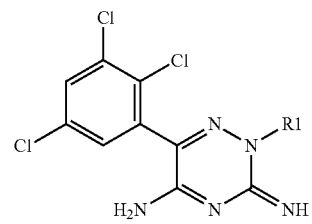

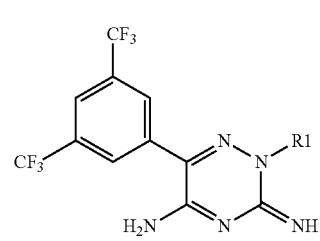

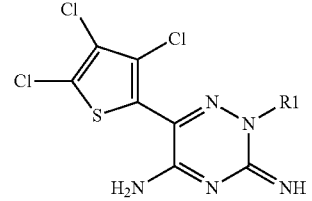

-continued

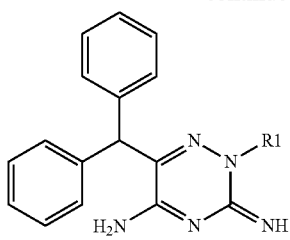

R₁ = —CH₂CCl₃
R₁ = —CH₂CHCl₂
R₁ = —CH₂CBr₃

CEN-216

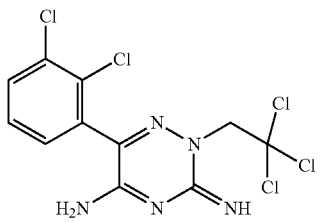

CEN-217

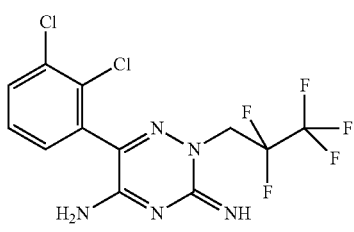

CEN-218

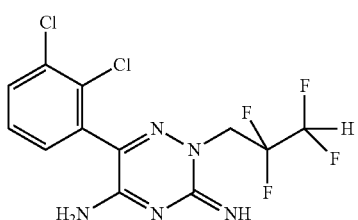

CEN-248

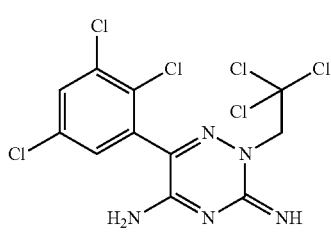

5(3)-Amino-6-(2,3-dichlorophenyl)-2,3(2,5)-dihydro-3(5)-imino-2-(2,2,2-trichloroethyl)-1,2,4-triazine trifluoromethanesulphonate [CEN-216]

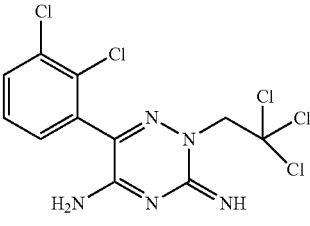

Triflate 3,5-Diamino-6-(2,3-dichlorophenyl)-1,2,4-triazine (Lamotrigine) (0.9 g; 3.50 mmole), 2,2,2-trichloroethyl triflate (1.0 g; 3.55 mmole), butan-2-one (10 cm³) and dimethylformamide (5 drops) were stirred at reflux for 25 hrs under nitrogen.

The solution was evaporated to dryness and the tan residue crystallised from acetone to give a fawn coloured microcrystalline powder. Yield=510 mg. Mpt—236-238, tlc (10% methanol-chloroform), Rf=0.38.

2,2,2-Trichloroethyl triflate

A mixture of 2,2,2-trichloroethanol (7.5 g; 0.05 mole) and triflic anhydride (14.1 g; 0.05 mole) was heated at 80° C. for 60 minutes.

After cooling to room temperature, the reaction mixture was diluted with ether (100 cm³) and extracted with ice cold 5% sodium hydrogen carbonate solution (3×50 cm³), dried over anhydrous sodium sulphate, filtered and evaporated to dryness in vacuo below 20° C. A colourless oil resulted. This solidified to colourless prisms on standing at 4° C. Yield=10.91 g (77.8%) Melting point 28-30° C. The product is used directly without further purification.

2,2,-Dichloroethyl triflate

A mixture of 2,2-dichloroethanol (5.75 g; 0.05 mole) and triflic anhydride (14.1 g; 0.05 mole) was heated at 80° C. for 60 minutes.

After cooling to room temperature, the reaction mixture was diluted with ether (100 cm³) and extracted with ice cold 5% sodium hydrogen carbonate solution (3×50 cm³), dried over anhydrous sodium sulphate, filtered and evaporated to dryness in vacuo below 20° C. A colourless oil resulted. The product is used directly without further purification.

2,2,2-Bromoroethyl triflate

A mixture of 2,2,2-trichloroethanol (14.15 g; 0.05 mole) and triflic anhydride (14.1 g; 0.05 mole) was heated at 80° C. for 120 minutes.

After cooling to room temperature, the reaction mixture was diluted with ether (100 cm³) and extracted with ice cold 5% sodium hydrogen carbonate solution (3×50 cm³), dried over anhydrous sodium sulphate, filtered and evaporated to dryness in vacuo below 20° C. A colourless solid resulted. Melting point 41-43° C. The product is used directly without further purification.

Biological Testing

Compounds of Formula (I) were tested for various activities as follows:

Screening Strategy

The screening strategy is designed to select compounds with appropriate sodium channel blocking activity and low side effect liability. To this end all compounds are processed through the primary sodium channel assay (veratrine-evoked uptake of [$^{14}$C]guanidine into rat forebrain synaptosomes) and IC$_{50}$ values computed from generated concentration-effect curves. In order to complement this data IC$_{50}$'s for selected compounds to inhibit binding of [$^3$H]BTX-B are also measured.

Previous studies have shown that substituted triazines are potential inhibitors of DiHydroFolate Reductase (DHFR) activity (McCullough and Bertino 1971, Cashmore et al, 1975, Booth et al, 1987) and Sapse et al, 1994). Inhibitors of DHFR (such as Methotrexate) have been used for the treatment of various cancers (Suster et al, 1978 and Niculescu-Duvaz et al, 1982) as inhibition of this enzyme interferes with cell growth but because of this effect (on cell growth) inhibitors of DHFR may also be teratogenic (Skalko and Gold, 1974, Feldcamp and Carey, 1993 and Buckley et al, 1997). Should compounds be found which are potent inhibitors of DHFR then such compounds may, themselves, have potential as anti-cancer agents. Several methods are available for measurement of inhibition of DHFR activity and for this study we have examined effects of compounds to inhibit the binding of [$^3$H] methotrexate (Myers et al, 1975 and Rothenberg et al, 1977).

Another common side-effect marker is inhibition of human Ether-a-go-go Related Gene potassium (hERG) potassium channel (Inward rectifying, I$_{Kr}$) activity which can be fatal due to heart failure brought about by development of long QT syndrome. A useful preliminary screen to assess potential to affect this channel is assessed by measurement of inhibition of the binding of [3H]astemizole to cell membranes expressing hERG. Selected compounds are tested for this activity by measurement of inhibition @ 10 μM. Assuming inhibition values lie between 10% and 90% it is possible to compute an extrapolated IC$_{50}$ for each compound.

The above screening cascade identifies compounds with appropriate sodium channel blocking activities that have a low(er) propensity for aforementioned side-effect liabilities. In order to develop these compounds further, some knowledge of their pharmacodynamic properties is required.

Sodium channel blockers, such as Sipatrigine, which both reduces the neurological deficit and infarct volume after middle cerebral artery occlusion in rats (Smith et al, 1997) and phenyloin, (which protect retinal ganglion cell death in an experimental model of glaucoma (Haim and Waxman, 2005) show neuroprotective efficacy in a range of models of nerve degeneration. As failure of oxygen supply compromises both glycolysis and oxidative phosphorylation, ischaemic damage ultimately leads to electrical failure (nerve signalling) and pump failure (restoration of cellular membrane potentials). These failures (of electrical and ion pump activity) are associated with decreased local concentrations of ATP (Astrup et al 1981). Thus the effect of compounds to maintain concentrations of ATP in 0.4 mm slices of rat hippocampus following a severe metabolic insult was used.

EXPERIMENTAL PROCEDURES

Preparation of Rat Forebrain Synaptosomes and Homogenates

Experiments were performed using forebrain (whole brain less cerebellum/medulla) from Male Wistar rats weighing 175-250 g. All efforts were made to reduce the number of animals used and all experiments were carried out in accordance with the UK Animals (Scientific Procedures) Act, 1986 and the European Community Council Directive of 24 Nov. 1986 (86/609/EEC). Following killing of animals by stunning and decapitation, the forebrain (whole brain less cerebellum/medulla) was rapidly dissected and transferred to a weighed tube containing ice-cold 0.25M sucrose.

Synaptosomes (heavy and light mitochondrial fraction containing synaptosomes) were prepared by transferring the forebrain (of known wet weight) to a glass Potter vessel to which 9 volumes ice-cold 0.25M sucrose had been added and homogenising, using a teflon pestle, by 8 'up and down strokes' of a Braun Potter S motor driven homogeniser set to 900 rpm. The resulting homogenate was centrifuged at 1036×g at 4° for 10 min and the supernatant collected. The remaining pellet was resuspended, as above, in fresh ice-cold 0.25M sucrose and the centrifugation step repeated. The supernatant fractions were pooled and centrifuged at 40,000×g (average) at 4° for 15 min and the resulting pellet resuspended in the appropriate assay buffer at a concentration of 20-25 mg wet weight per ml appropriate assay buffer.

Homogenates were prepared by transferring the known weight of forebrain to a cooled tube containing 9 volumes of ice-cold 50 mM pH 7.4 HEPES buffer. The mixture was homogenised @ 4° by 3×5 sec bursts of an Ultra-Turrax™ homogeniser set at maximum speed. The resulting homogenate was centrifuged at 40,000×g (average) at 4° for 15 min and the supernatant discarded. The resulting pellet was resuspended in 9 volumes of fresh ice-cold pH 7.4 buffer (as above), the centrifugation step was repeated and the resulting pellet resuspended in the [$^3$H]BTX-B binding buffer at a concentration of 20-25 mg wet weight per ml assay buffer.

[$^{14}$C] Guanidine Flux and Binding of [$^3$H]BTX-B

Both assays were carried out using 14 ml polypropylene test tubes to which a range of concentrations of the compounds under test were added. Test compounds were dissolved in DMSO and added to assays such that maximum concentration of DMSO did not exceed 2% v/v.

[$^{14}$C]Guanidine Flux:

The [$^{14}$C] guanidinine flux assay was measured using the method of Pauwels P J et al (1986) but carried out @ 30° for 2½ min.

REFERENCE

Pauwels P J, Leysen J E, Laduron P M. [3H]Batrachotoxinin A 20-alpha-benzoate binding to sodium channels in rat brain: characterization and pharmacological significance. Eur J. Pharmacol. 1986 May 27; 124(3):291-8.

Binding of [$^3$H]BTX-B

[$^3$H]BTX-B binding was carried out using the method described by Catterall et al (1981), except that both bovine serum albumin and TTX were omitted from the incubation medium.

REFERENCE

Catterall W A, Morrow C S, Daly J W, Brown G B. Binding of batrachotoxinin A 20-alpha-benzoate to a receptor site associated with sodium channels in synaptic nerve ending particles. J. Bio. Chem. 1981 Sep. 10; 256(17): 8922-7.

Binding of [$^3$H]Methotrexate

All steps were carried out at 4° (or on ice). Freshly dissected rat liver was dissected into 0.25M ice-cold Sucrose and subsequently homogenised (U-turrax) in 50 mM pH 6.0 phosphate buffer (10 ml/g tissue) containing 15 mM Dithiothreitol. The resulting homogenate was centrifuged @ 47,500×g for 20 min and supernatant (filtered through cotton wool to remove fatty lumps) stored @−80° before use (Rothenberg et al).

Inhibition of the binding of [$^3$H]methotrexate to rat liver homogenate supernatant fractions were carried out essentially as described by Arons et al, 1975. Results were calculated, either as IC$_{50}$ values (see below) derived from concentration-effect curves or as percentage inhibition values determined by comparison with control and cold Methotrexate (10 μM final concentration) binding values.

REFERENCE

Elliot Arons, Sheldon P. Rothenberg, Maria da Costa, Craig Fischer and M. Perwaiz Iqbal; Cancer Research 35, Aug. 1, 1975, 2033-2038, Computation of IC$_{50}$ Values Data are presented as mean±sem of number of experiments indicated in brackets. IC$_{50}$ values were obtained from radioligand displacement or guanidine flux inhibition curves by plotting log$_{10}$ concentration vs bound ligand/guanidine uptake according the equation:—

$$y = R\min + Rsp/\{1+\exp[-n(x-C)]\}$$

where
  y=bound (dpm)
  x=log$_{10}$ compound concentration
  Rmin=lower asymptote (i.e. 100% inhibition)
  Rsp=upper asymptote—Rmin (i.e. specific binding)
  n=slope (log$_e$)
  and C=IC$_{50}$ (i.e. concentration required to inhibit 50% of specific binding Hippocampal Slice Assay Neuroprotective efficacy was measured in 0.4 mm slices of rat hippocampus using the method described by Fowler and Li (1998)[1] except that Iodoacetate (400 μM)[2] was used as the metabolic insult. Compounds (usually 30 μM) were always directly compared with tetrodotoxin (1 μM)[3] for their ability to maintain slice concentrations of ATP following inhibition of glycolysis.

REFERENCES

1. Fowler J C, Li Y. Contributions of Na$^+$ flux and the anoxic depolarization to adenosine 5'-triphosphate levels in hypoxic/hypoglycemic rat hippocampal slices. Neuroscience 1998, 83, 717-722.
2. Reiner P B, Laycock A G, Doll C J. A pharmacological model of ischemia in the hippocampal slice. Neurosci Lett 1990; 119:175-8
3. Boening J A, Kass I S, Cottrell J E, Chambers G. The effect of blocking sodium influx on anoxic damage in the rat hippocampal slice. Neuroscience. 1989. vol 33 (2), 263-268.

Measurement of ATP and Protein

Individual slices were disrupted by ultra-sonication and the resulting homogenates centrifuged @ 10000×g for 5 min @ 4°. The supernatant was decanted into a fresh tube and any remaining supernatant removed by vacuum aspiration. The pellet was resuspended in 0.5 ml 0.1M KOH by ultra-sonication and the resulting suspensions warmed with gentle agitation @ 37° for 30 minutes.

Concentrations of ATP were measured in 6 μl of supernatant by mixing with Luciferase reagent (ATPLite from Perkin Elmer) and measuring subsequent luminescence in a 96-well plate Counter.

Protein concentration was measured using BCA™ protein assay (Pierce) with Bovine Serum albumin as reference standard.

ATP concentrations were expressed as nmoles/mg protein and neuroprotective indices (% protection) calculated by direct comparison with the effect of 1 μM TTX.

hERG:

Compounds were sent to MDS Pharma for measurement of their inhibition @ 10 μM concentration of the binding of [$^3$H]astemizole to HEK-293 cells expressing human recombinant hERG. Making the assumption that binding slopes would be 1.0 IC$_{50}$ values could be calculated (see above) for compounds exhibiting between 5% and 95% inhibition of binding.

L-Type Calcium Channels

Compounds were sent to MDS Pharma for measurement of their inhibition @ 10 concentration of the binding of [$^3$H] nitrendipine to rat cerebral cortex membranes. Making the assumption that binding slopes would be 1.0 IC$_{50}$ values could be calculated (see above) for compounds exhibiting between 5% and 95% inhibition of binding.

Rat Microsome Stability

Compounds were sent to BioFocus for measurement of their stability @ 1 μM concentration following incubation with rat liver microsomes for 40 minutes @ 37°.

MES Methodology (Maximal ElectroShock)

Male Wistar rats provided by BioLasco Taiwan (under Charles River Laboratories Technology Licensee) were used. Space allocation for 5 animals was 45×23×21 cm. Animals were housed in animal cages and maintained in a controlled temperature (21-23° C.) and humidity (50%-70%) environment with 12 hours light/dark cycles for at least three days in MDS Pharma Services—Taiwan Laboratory prior to use. Free access to standard lab chow for rats [MF-18 (Oriental Yeast Co., Ltd. Japan)] and reverse osmosis (RO) water were granted ad libitum. All aspects of this work including housing, experimentation and disposal of animals were performed in general accordance with the Guide for the Care and Use of Laboratory Animals (National Academy Press, Washington, D.C., 1996).

Test compounds were suspended/dissolved in 2% Tween 80 and dosed orally at a dose volume of 10 ml/Kg to groups of 5 Wistar male rats weighing 180+/−20 g, one hour before maximal electroshock (MES, 60 Hz sine wave, 150 mA, 200 msec duration) was applied through corneal electrodes. Appearance of maximal electroshock-induced tonic convulsions (MES) was determined for each animal. 50 percent or more (50%) inhibition of tonic convulsions by test substance indicates significant anticonvulsant activity.

Equipment/Chemicals:

Animal cage (Allentown, USA), Electronic shock generator (In-house, R. O. C.), Needle for oral administration (Natsume, Japan) and Rat scale (500 g, Yamato, Japan). Diphenylhydantoin sodium salt (Sigma, USA) and Tween 80 (Sigma, USA).

Test substances (CEN-216, CEN-145, CEN-148, CEN-152 and CEN-154) at 14, 42 or 100 mg/kg were administered orally to groups of 5 Wistar derived male rats weighing 180±20 g.

Results

Data from the various testing procedures is set out in the Table below:

Significance Criteria: >/=50% of max stimulation or Inhibition

Hippocampal Slice Data

| CEN nr | [$^{14}$C]guanidine flux Mean IC$_{50}$ (μM) | [$^3$H]mtx binding IC$_{50}$ (μM) (% inhibition @ 125 μM) | hERG % inhibition @ 10 μM | hERG IC$_{50}$ (μM) (extrapolated from 10 μM inh'n) | L-type Ca$^{2+}$ % inhibition @ 10 μM | L-type Ca$^{2+}$ IC$_{50}$ (μM) (extrapolated from 10 μM inh'n) | Microsome stability (human) % metabolized (40 min incubation 37°) |
|---|---|---|---|---|---|---|---|
| 1 (Ltg) | 219.2 | 631(17 ± 2(4)) 11** 68 *(***) | 1 | 989 | 17 | 48.8 | 20 |
| 216 | | | 12 | 73.3 | 27 | 27.0 | 0 |
| 217 | | | 28 | 25.7 | | | |
| 218 | | | 20 | 40.0 | | | |

* 99 μM

198 μM (*) uses fresh batch of supernatant

Inhibition of Binding of [3H]Batrachotoxinin Binding to Rat (Wistar) Brain

Data are presented as % inhibition @ 10 μM and extrapolated IC$_{50}$'s (which assumes hill slope=1).

Compounds which give <5% inhibition are ascribed IC$_{50}$'s of >200 μM

Compounds which give >95% inhibition are ascribed IC$_{50}$'s of <0.5 μM

Inhibition of Binding of [3H]BTX-B

| Compound | % inhibition (@ 10 μM) | Extrapolated IC50 (μM) |
|---|---|---|
| CEN-1 | −28 | >200 |
| CEN-216 | 42 | 13.8 |
| CEN-217 | 105 | <0.5 |
| CEN-218 | 108 | <0.5 |
| CEN-248 | 27 | 27 |

Summary of [3H]Batrachotoxinin Binding Method—279510

Sodium Channel, Site 2

Source: Wistar Rat brain

Ligand: 5 nM [.H] Batrachotoxin

Vehicle: 1% DMSO

Incubation Time/Temp: 60 minutes @ 37.0

Incubation Buffer: 50 mM HEPES, 50 mM Tris-HCl, pH7.4, 130 mM Choline Chloride, 5.4 mM KCl, 0.8 mM MgCl., 5.5 mM Glucose, 40 μg/ml LqTx $K_D$: 0.052 μM *

Non-Specific Ligand: 100 μM Veratridine

Bmax: 0.7 pmole/mg Protein *

Specific binding: 77%

Quantitation Method: Radioligand Binding

| Standard Compound | Conc'n (μM) | % protection (v 1 μM TTX) (mean ± sem) |
|---|---|---|
| TTX | 1 | 100 |
| Lamotrigine | 30 | 41 ± 5 (3) |
| [CEN-001] | | |
| DPH | 30 | 48 |

MES Results for N-Alkyl Substituted Triazines

| Compound | Dose (mg/kg po) | Results (% protection) |
|---|---|---|
| CEN-001 (Lamotrigine) | 25 | 100 |
| | 10 | 100 |
| | 3 | 60 |
| CEN-216 | 100 | 100 |
| | 30 | 100 |
| | 10 | 80 |
| | 3 | 0 |
| | 1 | 0 |
| CEN-217 | 100 | 60 |
| CEN-218 | 100 | 40 |
| CEN-248 | 30 | 100 |
| DiPhenylHydantoin | 100 | 80 |

(n = 5 rats)

| Compound No. | Structure | Nach ([3H]BTX-B) (extrapolated IC50 μM) | hERG ([3H]astemizole) (extrapolated IC50 μM) | Rat MES (anticonvulsant in vivo) (% protection @ mg/Kg (free base) po) | DHFR (% inhibition @ 125 μM) |
|---|---|---|---|---|---|
| CEN-216 | 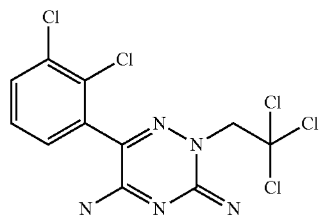 [SMILES: N=c1nc(N)c(-c2cccc(Cl)c2Cl)nn1CC(Cl)(Cl)Cl] | 20* | 50* | 80 @ 10 (ED50 = 9 mg/Kg po) (100% protection @ 72 mg/Kg (free base) po @ 1 h, 6 h and 24 h prior to mouse MES). (i.e. long duration of action following po dose in mouse) | 27 |
| CEN-217 | 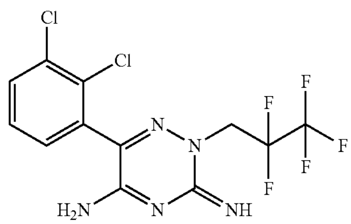 [SMILES: N=c1nc(N)c(-c2cccc(Cl)c2Cl)nn1CC(F)(F)C(F)(F)F] | <0.5 | 26 | 60 @ 100 | ND |
| CEN-218 | 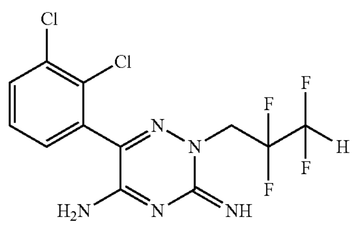 [SMILES: N=c1nc(N)c(-c2cccc(Cl)c2Cl)nn1CC(F)(F)C(F)F] | <0.5 | 40 | 40 @ 100 | ND |
| CEN-248 | 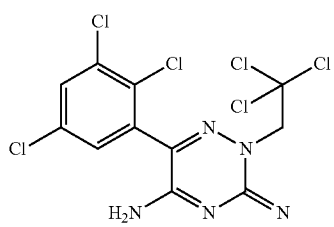 [SMILES: N=c1nc(N)c(-c2cc(Cl)cc(Cl)c2Cl)nn1CC(Cl)(Cl)Cl] | 27 | ND | 100% protection @ 30 | 87 |

CEN-216 extrapolated IC50 in L-type Calcium (phenylalkylamine site) binding assay = 27 μM
(CEN-001) Lamotrigine result using same enzyme prep @ 125 μM gave 26% inhibition In rat model of epilepsy (Maximal ElectroShock—MES), in which compounds were dosed orally one hour prior to 'shock', the ED50 (effective dose to protect 50% of rats from limb extension etc.) for CEN-216 is approx 9 mg/kg free base.

At 100 mg/kg free base in the above MES test CEN-217 and 218 gave 60% and 40% protection respectively i.e. ED50 for compounds of (very approx) 80 and 120 mg/kg free base respectively.

In mouse model of epilepsy (MES), compounds CEN-079 and CEN-216 were dosed orally (100 and 72 mg/kg free base respectively) @ 1 h, 6 h and 24 h prior to 'shock). Both compounds showed significant protection at all time points in that 100% protection was seen at all time points except that @ 24 h CEN-079 protective effect had reduced to 40% protection The screening data obtained in respect of representative compounds of the invention points to the suitability of compounds of general formula (I)) for treatment of disorders in mammals that are susceptible to sodium channel blockers and antifolates, and particularly disorders such epilepsy, multiple sclerosis, glaucoma and uveitis, cerebral traumas and cerebral ischaemias, stroke, head injury, spinal cord injury, surgical trauma, neurodegenerative disorders, motor neurone disease, Alzheimer's disease, Parkinson's disease, chronic inflammatory pain, neuropathic pain, migraine, bipolar disorder, mood, anxiety and cognitive disorders, schizophrenia and trigeminal autonomic cephalalgias; for treatment of mammalian cancers; and for treatment of malaria.

What is claimed is:

1. A compound according to formula (I):

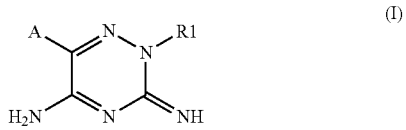

or a pharmaceutically acceptable salt or solvate thereof, wherein i) A is 2,3-dichlorophenyl and R1 is —CH₂CCl₃, —CH₂CF₂CF₃, or —CH₂CF₂CHF₂;
ii) A is 2,3,5-trichlorophenyl and R1 is —CH₂CCl₃, —CH₂CHCl₂, or CH₂CBr₃;
iii) A is 3,5,-bistrifluoromethylphenyl and R1 is —CH₂CCl₃, —CH₂CHCl₂, or CH₂CBr₃;
iv) A is bisphenyl methyl and R1 is —CH₂CCl₃, —CH₂CHCl₂, or CH₂CBr₃; or
v) A is 2-(3,4,5)-trichloro-bis-phenyl and R1 is —CH₂CCl₃, —CH₂CHCl₂, or CH₂CBr₃.

2. The salt of claim 1, wherein the salt is a mesylate salt.
3. The salt of claim 1, wherein the salt is an isethionate salt.
4. The salt of claim 1, wherein the salt is a triflate salt.
5. The compound of claim 1 or a pharmaceutically acceptable salt or solvate thereof, wherein the compound is one of the following compounds:

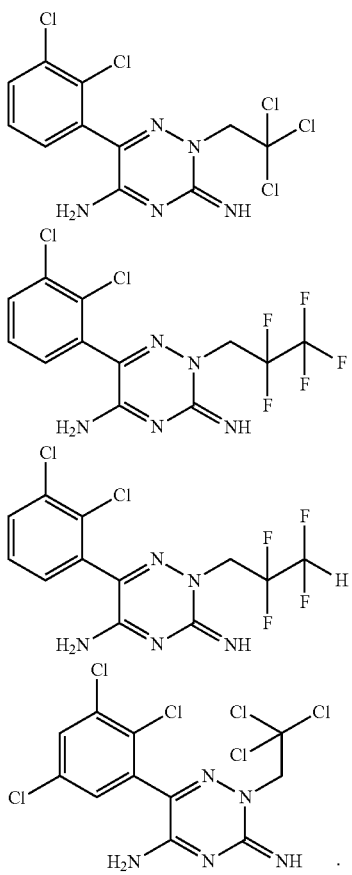

6. The compound of claim 5 or a pharmaceutically acceptable salt or solvate thereof, wherein the compound is:

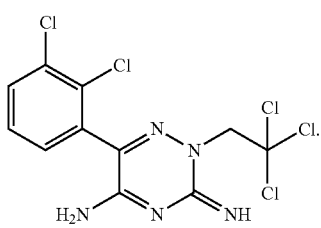 [SMILES: N=c1nc(N)c(-c2cccc(Cl)c2Cl)nn1CC(Cl)(Cl)Cl]

7. The salt of claim 6, wherein the salt is a mesylate salt.
8. The salt of claim 6, wherein the salt is an isethionate salt.
9. The salt of claim 6, wherein the salt is a triflate salt.
10. A compound according to formula (II):

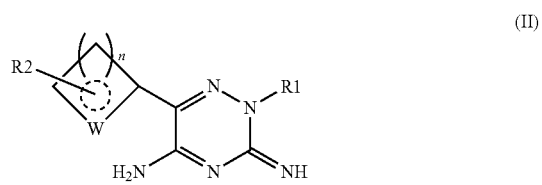

or a pharmaceutically acceptable salt or solvate thereof,
wherein R1 is a halo-alkyl group; W is sulphur, oxygen, or nitrogen; n is 1, 2 or 3; and R2 is one or more substituent groups.

11. The compound of claim 10 or a pharmaceutically acceptable salt or solvate thereof, wherein R2 is $NH_2$.

12. A pharmaceutical composition comprising a compound of claim 1 or a pharmaceutically acceptable salt or solvate thereof in a therapeutically effective amount and a pharmaceutically acceptable carrier.

13. A method of administering a therapeutically effective amount of a compound of claim 1 or a pharmaceutically acceptable salt or solvate thereof to a subject in need of treatment of epilepsy, multiple sclerosis, or neuropathic pain.

14. A pharmaceutical composition comprising the salt of claim 7 in a therapeutically effective amount and a pharmaceutically acceptable carrier.

15. A method of administering a therapeutically effective amount of the salt of claim 7 to a subject in need of treatment of epilepsy, multiple sclerosis, or neuropathic pain.

16. A pharmaceutical composition comprising the salt of claim 8 in a therapeutically effective amount and a pharmaceutically acceptable carrier.

17. A method of administering a therapeutically effective amount of the salt of claim 8 to a subject in need of treatment of epilepsy, multiple sclerosis, or neuropathic pain.

18. A pharmaceutical composition comprising the salt of claim 9 in a therapeutically effective amount and a pharmaceutically acceptable carrier.

19. A method of administering a therapeutically effective amount of the salt of claim 9 to a subject in need of treatment of epilepsy, multiple sclerosis, or neuropathic pain.

20. A pharmaceutical composition comprising a compound of claim 10 or a pharmaceutically acceptable salt or solvate thereof in a therapeutically effective amount and a pharmaceutically acceptable carrier.

21. A method of administering a therapeutically effective amount of a compound of claim 10 or a pharmaceutically acceptable salt or solvate thereof to a subject in need of treatment of epilepsy, multiple sclerosis, or neuropathic pain.

* * * * *